United States Patent [19]

Giordano et al.

[11] Patent Number: 4,642,376
[45] Date of Patent: Feb. 10, 1987

[54] PROCESS FOR THE PREPARATION OF ALPHA-HYDROXYARYL-ALKANOIC ACIDS

[75] Inventors: Claudio Giordano, Vicenza; Fulvio Uggeri, Codogno; Francesco Minisci, Milan, all of Italy

[73] Assignee: Zambon S.p.A, Vicenza, Italy

[21] Appl. No.: 697,450

[22] Filed: Feb. 1, 1985

[30] Foreign Application Priority Data

Feb. 3, 1984 [IT] Italy ................. 19438 A/84

[51] Int. Cl.$^4$ ............. C07C 65/24; C07C 43/30
[52] U.S. Cl. .................... 562/466; 562/470; 562/478; 549/369; 568/592
[58] Field of Search .......... 562/466, 470, 478; 549/369; 568/592

[56] References Cited

U.S. PATENT DOCUMENTS 4,542,237 9/1985 Schloemer ................. 562/466

Primary Examiner—Paul J. Killos
Attorney, Agent, or Firm—Cushman, Darby & Cushman

[57] ABSTRACT

A process is described for the preparation of alpha-hydroxyl-alkanoic acids of formula

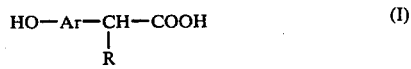

which are known anti-inflammatory agents or intermediates for known pharmaceutical products. The process consists essentially in the rearrangement of phenolates of formula

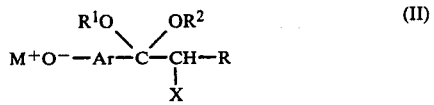

wherein Ar is an unsubstituted or substituted phenyl or naphthyl, in aqueous environment or in an organic medium, at temperatures comprised within the range of from 0° to 100° C. and within short times, followed by either acid or alkaline hydrolysis.

7 Claims, No Drawings

PROCESS FOR THE PREPARATION OF ALPHA-HYDROXYARYL-ALKANOIC ACIDS

DISCLOSURE

The present invention relates to a new process for the preparation of alpha-hydroxyaryl-alkanoic acids of formula $$HO-Ar-\underset{R}{CH}-COOH \quad (I)$$

wherein
Ar=phenyl or naphthyl, possibly substituted with $C_1$-$C_3$ alkyl; OH; $C_1$-$C_3$ alkoxyl; halogen or phenyl; and
R=H, $C_1C_6$ straight or branched alkyl.

Alpha-hydroxyaryl-alkanoic acids of formula (I) are known anti-inflammatory agents (U.S. Pat. No. 3,978,116), or they are useful intermediates in the synthesis of known products having therapeutical action.

As an example, the ester of 2-(4'-hydroxyphenyl)-acetic acid is the intermediate in the synthesis of Atenolol (β-blocker); 2-(3'-chloro-4'-hydroxyphenyl)-acetic acid is the intermediate in the synthesis of Alclofenac (anti-inflammatory product); 2-(2'-hydroxyphenyl)-acetic acid is the intermediate in the synthesis of Fenclofenac (anti-inflammatory agent); 2-(4'-hydroxy-3'-methoxyphenyl)acetic acid is an intermediate in the synthesis of Propanidid (anesthetic agent); 2-(3'-hydroxyphenyl)-propionic acid is the intermediate in the synthesis of Fenoprofen (anti-inflammatory agent); 2-(6'-hydroxy-2'-naphthyl)-propionic acid is the intermediate in the synthesis of Naproxen (anti-inflammatory agent).

In particular, this latter product is obtained by simple etherification of 2-(6'-hydroxy-2'-naphthyl)-propionic acid of formula (I).

The new process according to the present invention for preparing the compounds of formula (I) is essentially based on the following reaction:

$$\overset{+\ -}{M}O-Ar-\underset{X}{\overset{R^1O\diagdown\diagup OR^2}{C}}-\underset{}{CH}-R \longrightarrow HO-Ar-\underset{R}{CH}-COOH$$

$$(II) \qquad\qquad\qquad\qquad (I)$$

wherein:
Ar and R are as defined hereinabove;
$R_1$ and $R_2$, equal or different, are a $C_1$-$C_6$ alkyl group, $C_3$-$C_6$ alkenyl or alkynyl group, or bound together form a saturated or unsaturated heterocyclic ring, comprising from 3 to 7 carbon atoms;
X=Cl, Br, I;
M=counter-ion of the phenolate, preferably selected from the group consisting of alkaline and alkaline-earth cations; tetraalkylammonium, tetraalkylarsonium and tetraalkylphosphonium groups.

Therefore, the new process consists essentially in the rearrangement of ketals (II), comprising a leaving group in alpha to the ketal group, and containing a phenolate group on the aryl radical, followed by hydrolysis for liberating the acids (I).

The rearrangement of ketals (II) is accomplished within short times, at temperatures comprised within the range of from 0° to 100° C., in aqueous or in organic medium. Processes have already been described for the preparation of alpha-aryl-alkanoic acids by means of the rearrangement of ketals.

The European Patent Application No. 81200210.3 discloses indeed a process for the preparation of alpha-aryl-alkanoic acids by means of the rearrangement of ketals of formula $$Ar-\underset{X}{\overset{R'O\diagdown\diagup OR''}{C}}-CH-R'''$$

in which X=Halogen, R', R", R'''=alkyl radicals, and Ar=aryl radical, in the presence of a Lewis' acid. In this case, the end product is polluted by salts of heavy metals used as the catalysts, and difficulty separable.

The European Patent Application No. 81304154.8 discloses a process similar to the one previously shown, which uses as starting products ketals of formula $$Ar-\underset{OSO_2R_5}{\overset{R^3O\diagdown\diagup OR^4}{C}}-CH-R_1$$

wherein $R^1$, $R^3$, $R^4$, $R^5$=alkyl groups, and Ar=aryl radical, and causes the rearrangement to take place either by hydrolysis with water, under neutral or basic conditions, at high temperatures, or by means of the addition of a compound showing affinity for oxygen, selected among Lewis' acids and trialkylsilyl derivatives.

This process requires always long times and high temperatures, and, should compounds having affinity for oxygen be used, it shows the problem of end product purification.

According to the known processes, Ar could also be a substituted aryl radical, but in no case do such processes claim the use of substituents of the phenolate type. The Applicants have now quite unforeseeable found that when aryl-alkyl-ketals comprise in their aryl group a substituent of the phenolate type, it is possible to carry out the rearrangement thereof to alpha-aryl-alkanoic acids at low temperatures, always lower than 100° C., and within short times, without the addition of any kind of promoters.

Under the conditions of temperatures and times, under which the rearrangement reaction is accomplished of ketals of formula (II), the corresponding ketals without substituents on the aryl group, or with substituents of different nature and in particular containing ether groups, do not show the rearrangement, or are rearranged to a negligible extent.

It is immediately evident the usefulness from the industrial viewpoint of a process which takes place under extremely mild reaction conditions, and without the addition of foreign substances, being impurities for the end product.

Also the reaction medium, in the new process according to the present invention, appeared quite unforeseeable to be not critical, it being possible to operate as well in water or in a protic or aprotic, polar or not polar organic solvent.

Compounds of formula

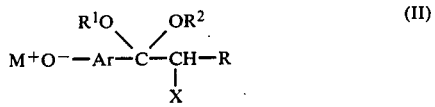

(II)

in which Ar, R, $R^1$, $R^2$, X, M are as hereinabove defined, are new compounds.

They can be prepared by salification of corresponding hydroxy-aryl-alkyl-ketones under suitable conditions, followed by ketalization, or directly by salification of hydroxy-aryl-alkyl-ketals.

Preferably, according to the present invention, they are prepared directly inside the reaction mixture within which the rearrangement is carried out.

It is therefore another aspect of the invention, constituting a preferred embodiment thereof, the preparation of compounds (II) starting from compounds of formula

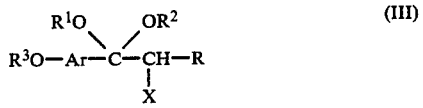

(III)

wherein $R^3$=H, —$COR^4$, —$SO_2R^5$, —$Si(R^6)_3$, with $R^4$ and $R^6$ being the same or different to each other, and equal to straight or branched $C_1$-$C_4$ alkyl, and $R^5$=—$CH_3$ or —$C_6H_4$—$CH_3$; and however $R^3$=group capable of being displaced by the phenolic hydroxyl in a basic environment ( T. W. Green "Protective Groups in Organic Synthesis", 1981, Wiley and Sons); R, Ar and X being as defined hereinabove; by means of the addition of a strong base, capable of salifying the phenolic hydroxyl, and of the subsequent direct rearrangement of phenolates of formula (II) formed in the reaction mixture to hydroxyaryl-alkanoic acids of formula (I), without the intermediate separation thereof.

In that case, the process is schematically shown by the following total reaction

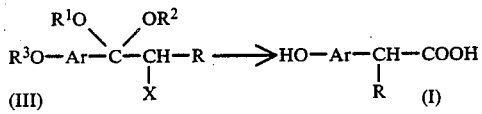

wherein R, $R^1$, $R^2$, $R^3$, Ar, X are as defined previously. This total reaction is however accomplished by rearranging the ketals in the presence of strong bases, under very mild conditions, i.e., at temperatures comprised within the range of from 0° to 100° C., and within relatively short times, and carrying out an acid or alkaline hydrolysis directly on the reaction mixture.

Practically, the process according to the present invention, in its preferred embodiment, comprises the treatment of compounds of formula (III), with an at least stoichiometric amount of a salifying base.

As suitable bases for the accomplishment of the new process the hydroxides, the alkoxides, the carbonates, the bicarbonates, the hydrides of alkaline metals or of alkaline-earth metals can be mentioned, as well as the tetraalkylammonium, tetraalkylarsonium or tetraalkylphosphonium bases.

As previously mentioned, the reaction medium can be water or an organic solvent, suitably selected depending on the ketal to be dissolved, and on the base to be used. It is necessary indeed that the base-solvent system be of such an alkalinity, as to ensure the transformation of —OH or —$OR^3$ group into —$O^-$ $M^+$ phenolate group, which is critically necessary for the accomplishment of the process according to the invention.

Particularly suitable solvents are, in addition to water, methanol, ethanol, benzene, toluene, DMF, THF, dichloroethane and similar products, however with no particular limitations, but those deriving from the nature of the system.

When the rearrangement is ended, a base or an acid is added to the reaction mixture, to the purpose of hydrolyzing the product obtained, in case of alkaline hydrolysis the salt of the acid is obtained, in case of acid hydrolysis the free acid is obtained.

In any case, the end product is formed with high yields, and it can be easily isolated at a high purity level from the reaction mixture, by means of normal separation techniques, by extraction and precipitation from suitable solvents.

α-Substituted hydroxyaryl-ketals of formula (III), wherein the hydroxyl is free or protected by the radical $R^3$, are prepared by conventional methods, even if many of them are novel products. In general, the radical X is first selectively introduced in chain in corresponding hydroxyaryl-alkyl-ketones, by means of suitable halogenating agents, and the products obtained are then transformed into their ketals by reaction with an alcohol or with a glycol, selected according to the definitions given heretofore for $R^1$ and $R^2$.

It must however be noted that the presence of an hydroxyl, free or protected with a group labile in alkaline environment, on the aryl radical of aryl-alkyl-ketone, renders these compounds particularly reactive, so that both the halogenation step (or however the step of substitution in the α-position) and the subsequent ketal formation step proceed in a particularly favourable way from the viewpoint of selectivity, in the case of halogenating in chain, as well as from the view point of reaction times and temperatures, in the case of ketal formation. To the purpose of better evidencing the operating modalities of practical realization of the new process according to the present invention, and of consequently making easier the reproduction thereof, hereunder some significant Examples are reported, which are not to be constructed as being in any way limitative of claimed domain. For sake of completeness, also the practical modalities are reported of preparation of the precursors of compounds of formula (II), also because, as it has already been mentioned, the presence of the free or protected hydroxyl group on the aryl radical allowed also the steps of halogenating and of ketalization of the ketones to be advantageously modified.

EXAMPLE 1

Preparation of 2-(4'-hydroxyphenyl)-propionic acid (a) Ketone bromination

A mixture of 4'-hydroxypropiophenone (175 g; 1.16 mole), tetrabutylammonium prebromide (641.65 g; 1.33 mole) in tetrahydrofuran (2.3 l) is heated at 40° C., while being stirred under a nitrogen atmosphere for 8 hours. The mixture is then poured into water (5 l) and extracted with toluene. The toluenic extract is washed with water, dried on sodium sulphate, and the solvent is evaporated. The oily residue is crystallized from a 1/1 methylene chloride/hexane mixture, to give 2-bromo-(4'-hydroxyphenyl)-propan-1-one (203 g; 0.88 mole; yield of 76%). Melting point 95°-97° C.

¹H-NMR (CDCl₃ TMS) ppm: 1.9 (d, 3H, J=7 Hz); 5.4 (q, 1H, J=7 Hz); 5.9 (s, 1H broad); 6.9–8.3 (AB q, 4H); 60 MHz equipment.

I.R.: C═O stretching 1.660 cm⁻¹ (nujol).

(b) Br-Keton ketalization

A mixture of 2-bromo-(4'-hydroxyphenyl)-propan-1-one (40 g; 0.147 mole), 2,2-dimethyl-1,3-propanediol (36.32 g; 0.348 mole), p-toluenesulphonic acid (1.74 g; 0.009 mole) in toluene (175 ml) is refluxed, while azeotropically distilling off the water being formed during the reaction. The reaction is complete after 4 hours. The mixture is cooled to room temperature and poured into a 10% aqueous solution of sodium bicarbonate (500 ml); the organic phase is separated and the water phase is extracted with toluene. The organic phase and the toluene extracts are combined and dried on sodium sulphate, and the solvent is evaporated. The residue is crystallized from a 1/1 hexane/ethyl ether mixture to give 2-(1'-bromoethyl)-5,5-dimethyl-2'(4'-hydroxyphenyl)-1,3-dioxane (32 g; 0.10 mole; yield of 70%). Melting point 115°–118° C.

¹H-NMR (CDCl₃ TMS) ppm: 0.6 (s, 3H); 1.4 (s, 3H); 1.6 (d, 3H J=7 Hz); 3.45 (s, 2H); 3.5 (s, 2H); 4.2 (q, 1H J=7 Hz); 5.4 (s, broad 1H); 6.8–7.5 (AB q, 4H J=7 Hz); 60 MHz equipment.

I.R.: C═O stretching absent.

(c) Ketal rearrangement and hydrolysis

A solution of sodium methoxide (0.012 mole) is prepared by adding at room temperature metallic sodium (0.276 g; 0.012 mole) to methanol (100 ml) under a nitrogen blanket.

To the so-obtained solution, 2-(1-bromoethyl)-5,5-dimethyl-2-(4'-hydroxyphenyl)-1,3-dioxane (3.5 g, 0.011 mole) is added, and the reaction mixture is kept stirred at room temperature for two hours.

The reaction mixture is then poured into a 1N solution of hydrochloric acid (100 ml) and extracted with ethyl ether.

The ethereal phase is evaporated and the residue is treated with a 20% aqueous solution of KOH (50 ml), while being refluxed and stirred for two hours. The reaction mixture is cooled to room temperature, and is then made acid to pH 1 with concentrated HCl, and extracted with ethyl ether. The organic phase is extracted with a 10% aqueous solution of sodium bicarbonate. The aqueous phase is made acid to pH 1 with concentrated HCl, and extracted with ethyl ether. The ethereal extract is dried on anhydrous sodium sulphate, and evaporated under vacuum to give 2-(4'-hydroxyphenyl)-propionic acid (1.5 g; 0.009 mole; yield of 82%). Melting point 128°–129° C.

¹H-NMR (acetone d₆ TMS) ppm: 1.4 (d, 3H J=7 Hz); 3.7 (q 1H J=7 Hz); 6.75=7.4 (AB q 4H); 7.3–8.3 (1H broad); 60 MHz equipment.

I.R.: C═O stretching 1.710 cm⁻¹.

COMPARISON EXAMPLE

A mixture of 2-(1'-bromoethyl)-5,5-dimethyl-2-(4'-hydroxyphenyl)-1,3-dioxane (1.75 g; 0.006 mole) and 2-(1'-bromoethyl)-5,5-dimethyl-2-(4'-methoxyphenyl)-1,3-dioxane (1.97 g; 0.006 mole) is added to a solution of sodium methoxide (0.024 mole) in methanol (100 ml). The so-obtained solution is maintained at 25° C. while being stirred under a nitrogen atmosphere. After 2 hours, 2-(1'-bromoethyl)-5,5-dimethyl-2-(4'-hydroxyphenyl)-1,3-dioxane is converted by more than 90% (TLC and NMR analysis), whereas 2-(1'-bromoethyl)-5,5-dimethyl-2-(4'-methoxyphenyl)-1,3-dioxane has remained unchanged (TLC and NMR analysis).

The reaction mixture is then poured into a 10% solution of sodium carbonate (100 ml), and extracted with ethyl ether.

The ethereal solution is evaporated, and the residue is hydrolyzed as described in Example 1c, to give 2-(4'-methoxyphenyl)-propionc acid (0.13 g; 0.00072 mole; yield of 1%). 99% Of 2-(1'-bromoethyl)-5,5-dimethyl-2-(4'-methoxyphenyl)-1,3-dioxane was recovered unchanged. The aqueous solution, which had been stored, is made acid to pH 1 with concentrated HCl and extracted with ethyl ether. Ethereal solution is evaporated and the residue is hydrolyzed as in Example 1c, to give 2-(4'-hydroxyphenyl)-propionic acid (0.92 g; 0.055 mole; yield of 92%).

EXAMPLE 2

Preparation of 2-(4'-hydroxyphenyl)-propionic acid

To a solution of potassium hydroxide (0.185 g; 0.0039 mole) in water (18 ml), 2-(1'-bromoethyl)-5,5-dimethyl-2-(4'-hydroxyphenyl)-1,3-dioxane (1 g, 0.0031 mole) is added, and the mixture is kept under a nitrogen atmosphere at room temperature for 30 minutes. After this time, potassium hydroxide (0.5 g; 0.089 mole) is added, and the mixture is refluxed for 1 hour. The reaction mixture is then submitted to successive treatments with HCl, with NaHCO₃ and once again with HCl as described in Example 1c. 2-(4'-Hydroxyphenyl)-propionic acid is obtained (0.385 g; 0.0023 mole; yield of 75%). Its characteristics are identical to those given for the product of Example 1.

EXAMPLE 3

Preparation of 2-(4'-hydroxyphenyl)-propionic acid

A mixture of 2-(1'-bromoethyl)-5,5-dimethyl-2-(4'-hydroxyphenyl)-1,3-dioxane (3.15 g; 0.01 mole), potassium carbonate (6.8 g; 0.05 mole), tetrabutylammonium bromide (0.06 g; 0.0002 mole) in dimethylformamide (30 ml) is heated while being stirred for 36 hours at 90° C. The mixture is then cooled to room temperature, poured into a 1N solution of HCl (300 ml), and extracted with toluene. The organic phase is evaporated and the residue is hydrolyzed as in Example 1c, to obtain 2-(4'-hydroxyphenyl)-propionic acid (0.49 g; 0.003 mole; yield of 30%). The characteristics of the acid are identical to those of Example 1.

EXAMPLE 4

Preparation of 2-(4'-hydroxyphenyl)-propionic acid

To a suspension of sodium hydride (0.024 g; 0.001 mole) in anhydrous tetrahydrofuran (3 ml), a solution of 2-(1'-bromoethyl)-5,5-dimethyl-2-(4'-hydroxyphenyl)-1,3-dioxane (0.315 g; 0.001 mole) in anhydrous tetrahydrofuran (2 ml) is added under an inert atmosphere, at room temperature. The reaction mixture is refluxed for 24 hours. The solvent is then removed by evaporation under vacuum at room temperature. The residue is submitted to chromatography on silica gel (elutant: 1/1 hexane/ether). The fraction with Rf comprised within 0.4 and 0.1 is collected, and is hydrolyzed as described in Example 1c, to give 2-(4'-hydroxyphenyl)-propionic acid (0.06 g; 0.0004 mole; yield of 40%).

Its characteristics are identical to those shown in Example 1.

EXAMPLE 5

Preparation of 2-(4'-hydroxyphenyl)-propionic acid

A mixture of 2-(1'-bromoethyl)-5,5-dimethyl-2-(4'-hydroxyphenyl)-1,3-dioxane (3.15 g; 0.01 mole), potassium carbonate (6.8 g; 0.05 mole), tetrabutylammonium bromide (0.06 g; 0.0002 mole) in toluene (30 ml) is heated under stirring for 36 hours at 90° C. The mixture is then poured into a 1N hydrochloric acid solution (300 ml), the organic phase is separated and the aqueous phase is extracted again with toluene. The organic phases are combined, and the residue is hydrolyzed as in Example 1c to obtain 2-(4'-hydroxyphenyl)-propionic acid (0.49 g; 0.003 mole; yield of 30%). The characteristics of the product are identical to those given in Example 1.

EXAMPLE 6

Preparation of 2-(6'-hydroxy-2'-naphthyl)-propionic acid (a) Ketone bromination

To a mixture of 1-(6'-acetoxy-2'-naphthyl)-propan-1-one (100 g, 0.413 mole) in methylene chloride (1.052 ml) bromine (659 g; 0.413 mole) is added dropwise over about 1 hour at room temperature. The mixture is kept stirred at room temperature for another 2 hours, and is then poured into water (2 l); the organic phase is separated, washed with a 10% solution of sodium tiosulphate (100 ml), then dried on sodium sulphate, and the solvent is evaporated in vacuo. The residue is 2-bromo-1-(6'-acetoxy-2'-naphthyl)-propan-1-one (129.3 g; 0,4 mole; yield of 97%). Melting point 96°–97° C. (MeOH).

A solution of 2-bromo-1-(6'-acetoxy-2'-naphthyl)-propan-1-one (1 g; 0.003 mole), sodium bicarbonate (10 ml of 10% aqueous solution) in methanol (30 ml) is kept stirred for 8–10 hours at room temperature.

The mixture is then diluted with water (100 ml) and extracted with ether. The ethereal extract is desiccated and the solvent is evaporated in vacuo.

The residue is 2-bromo-1-(6'-hydroxy-2'-naphthyl)-propan-1-one (0.6 g; 0.002 mole; yield of 70%). Melting point 125°–127° C.

$^1$H-NMR (CDCl$_3$-TMS) ppm: 1.9 (d, 3H); 5.5 (q, 1H); 6.9–8.7 (m, 7H); 60 MHz equipment.

I.R.: C=O stretching 1.665 cm$^{-1}$.

(b) Br-Ketone ketalization

A mixture of 2-bromo-1-(6'-hydroxy-2'-naphthyl)-propan-1-one (2 g; 0.007 mole), 2,2-dimethyl-1,3-propanediol (1.42 g; 0.014 mole), p-toluenesulphonic acid (0.167 g; 0.0008 mole), toluene (15 ml) is refluxed for 4 hours, while distilling off the water being formed during the reaction, by means of a suitable fraction separating unit (Dean and Stark apparatus).

The mixture is then cooled to room temperature and poured into a 10% aqueous solution of sodium carbonate (100 ml) and extracted with toluene. The residue is purified on a chromatographic column (elutant 1/1 hexane/ether).

The most mobile product is 2-(1'-bromoethyl)-5,5-dimethyl-2-(6'-hydroxy-2'-naphthyl)-1,3-dioxane (1.80 g, after evaporation of eluted solvent; 0.0049 mole; yield of 70.5%). Melting point 134°–135° C.

$^1$H-NMR (CDCl$_3$-TMS) ppm: 0.5 (s, 3H); 1,3 (s, 3H); 1.6 (d, 3H; J=7 Hz); 3.55 (m, 4H); 4.2 (q, 1H; J=7 Hz); 5.2 (1H broad); 7.1–7.9 (m, 6H); 200 MHz equipment.

I.R.: C=O stretching absent.

(c) Ketal rearrangement and hydrolysis

A solution of sodium methoxide is prepared by adding metallic sodium (0.023 g; 0.01 mole) to methanol (100 ml) under a nitrogen blanket, at room temperature. To the so-obtained solution, 2-(1'-bromoethyl)-5,5-dimethyl-2-(6'-hydroxy-2'-naphthyl)-1,3-dioxane (3.65 g; 0.01 mole) is added, and the whole is heated at 55° C. for 12 hours. Reaction mixture is then poured into a 1N solution of hydrochloric acid (100 ml), and extracted with ether. The ethereal extract is evaporated and the residue is treated with a mixture of methanol (170 ml) and 40% aqueous solution of KOH (30 ml) at room temperature, for 5 hours. Methanol is then evaporated in vacuo, and the residue is diluted with water (200 ml). The so-obtained solution is extracted with ethyl ether and the aqueous phase is made acid to pH 1 with concentrated HCl, and extracted with ether. The ethereal phase is dried on anhydrous sodium sulphate and the solvent is evaporated in vacuo. The residue obtained is 2-(6'-hydroxy-2'-naphthyl)propionic acid (1.81 g; 0.0083 mole; yield of 80%). Melting point 170°–175° C.

COMPARISON EXAMPLE

A solution of sodium methoxide (0.0054 mole) is prepared by adding metallic sodium (0.125 g; 0.0054 mole) to methanol (50 ml) under nitrogen at room temperature. To so-obtained solution, 2-(1'-bromoethyl)-5,5-dimethyl-2-(6'-hydroxy-2'-naphthyl)-1,3-dioxane (1.8 g; 0.005 mole) is added, and the solution is heated to 55° C.

In a parallel run, to a solution of sodium methoxide (0.0054 mole) prepared as previously described, 2-(1'-bromoethyl)-5,5-dimethyl-2-(6'-methoxy-2'-naphthyl)-1,3-dioxane (1.9 g; 0.005 mole) is added, and the reaction mixture is heated to 55° C.

The course of the two reactions is followed by NMR and TLC as a function of time.

After 10 hours, 2-(1'-bromoethyl)-5,5-dimethyl-2-(6'-hydroxy-2'-naphthyl)-1,3-dioxane is converted by more than 90% and, when hydrolyzed as described in Example 2a, it gives 2-(6'-hydroxy-2'-naphthyl)-propionic acid (0.85 g; 0.039 mole), yield of 78.7%.

After the same time, 2-(1'-bromoethyl)-5,5-dimethyl-2-(6'-methoxy-2'-naphthyl)-1,3-dioxane remains unchanged in the reaction mixture, and is recovered by more than 90%.

EXAMPLE 7

Preparation of 2-(6'-hydroxy-2'-naphthyl)-propionic acid (a) Br-Ketone ketalization A mixture of 2-bromo-1-(6'-acetoxy-2'-naphthyl)-propan-1-one (8.77 g; 0.027 mole), trimethylorthoformate (8.59 g; 0.081 mole), methanesulphonic acid (0.4 ml), methanol (50 ml) is heated at 55° C. for 10 hours. The mixture is then cooled to room temperature, poured into a 10% aqueous solution of sodium bicarbonate (250 ml) and extracted with methylene chloride. The organic phase is desiccated on sodium sulphate, and the solvent is evaporated under vacuum. The residue is 2-bromo-1,1-dimethoxy-1-(6'-hydroxy-2'-naphthyl)-propane (8 g; 0.024 mole; yield of 90%); melting point 108°–110° C.

$^1$H-NMR (CDCl$_3$-TMS) ppm: 1.6 (d, 3H); 3.3 (s, 3H); 3.5 (s, 3H); 4.6 (q, 1H); 5.5 (s, 1H); 7.1–8.2 (m, 6H); 60 MHz equipment.

I.R.: C=O stretching absent.

(b) Ketal rearrangement and hydrolysis

A mixture of 2-bromo-1,1-dimethoxy-1-(6'-hydroxy-2'-naphthyl)-propane (1.5 g; 0.0046 mole), potassium hydroxide (0.279 g; 0.005 mole) and methanol (20 ml) is heated at 55° C. for 3 hours. The mixture is then poured into water (100 ml), made acid to pH 5 with acetic acid, and extracted with ether.

The ethereal extract is desiccated on sodium sulphate, and the solvent is evaporated. The residue is hydrolyzed as in Example 6c. 2-(6'-Hydroxy-2'-naphthyl)-propionic acid (0.51 g; 0.0026 mole; yield of 51.3%) is obtained. Melting point 170°–176° C.

EXAMPLE 8

Preparation of 2-(6'-hydroxy-2'-naphthyl)-propionic acid

A mixture of 2-(1'-bromoethyl)-5,5-dimethyl-2-(6'-hydroxy-2'-naphthyl)-1,3-dioxane (0.91 g; 0.0024 mole), potassium hydroxide (0.164 g; 0.0029 mole), water (25 ml), methanol (40 ml) is heated at 55° C. for 8 hours. The mixture is then cooled to room temperature, poured into water (150 ml), made acid to pH 4–5 with acetic acid and extracted with ethyl ether.

The ethereal phase is dried on sodium sulphate and the solvent is evaporated. The residue is hydrolyzed as in Example 6c. 2-(6'-Hydroxy-2'-naphthyl)-propionic acid is obtained (0.43 g; 0.0020 mole; yield of 82%). Melting point 170°–175° C.

EXAMPLE 9

Preparation of 2-(6'-methoxy-2'-naphthyl)-propionic acid

To a mixture of 2-(6'-hydroxy-2'-naphthyl)propionic acid (1 g; 0.0046 mole), sodium hydroxide (0.4 g; 0.1 mole), water (4 ml) cooled at 10° C., dimethyl sulphate (0.63 g; 0.005 mole) is added.

The mixture is refluxed for 2 hours, it is then cooled to room temperature, and diluted with water (50 ml). It is then extracted with ethyl ether and the aqueous phase is made acid to pH 1 with concentrated hydrochloric acid and extracted again with ethyl ether.

The ethereal phases are combined, dried on anhydrous sodium sulphate, and the solvent is evaporated in vacuo. The residue is 2-(6'-methoxy-2'-naphthyl)-propionic acid (0.961 g; 0.0417 mole; yield of 91%). Melting point 153°–154° C.

We claim:

1. Process for the preparation of alpha-hydroxyaryl-alkanoic acids of formula

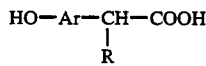

wherein Ar=phenyl or naphthyl, unsubstituted or substituted with $C_1$–$C_3$ alkyl; OH or $C_1$–$C_3$ alkoxy; halogen or phenyl
and R=H, straight or branched $C_1$–$C_6$ alkyl, characterized in that the rearrangement is carried out in an aqueous medium or in an organic solvent, at temperatures of from 0° to 100° C., of ketals of formula

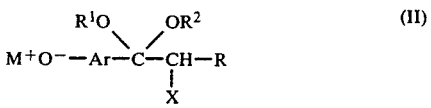

wherein Ar and R are as defined above;
$R_1$ and $R_2$, equal or different, are a $C_1$–$C_6$ alkyl group, a $C_3$–$C_6$ alkenyl or alkynyl group, or bound together, form a saturated on unsaturated heterocyclic ring, comprising from 3 to 7 carbon atoms; X=Cl, Br, I; M=counter-ion of the phenolate, and that the product obtained is submitted to hydrolysis, without being separated from the reaction mixture.

2. Process as claimed in claim 1, in which the counter-ion of phenolate M is selected from the group consisting of alkaline and alkaline-earth cations, tetraalkylammonium, tetraalkylarsonium and tetraalkylphosphonium groups.

3. Process as claimed in claim 1, in which the organic solvent can be protic or aprotic, polar or not polar.

4. Process as claimed in claim 1, in which the hydrolysis is carried out by means of an acid or of a base, the acid (I) being anyway separated after an acidifying end stage.

5. Process as claimed in claim 1, wherein the ketal (II) is directly formed within the reaction mixture by treatment of a compound of formula

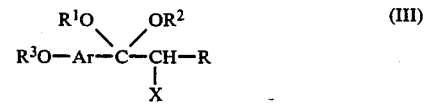

wherein Ar, R, $R^1$, $R^2$, X are as defined above, and $R^3$=H, —COR$^4$, —SO$_2$R$^5$, —Si(R$^6$)$_3$, with $R^4$ and $R^6$ being the same or different to each other, and equal to $C_1$–$C_4$ straight or branched-chain alkyl, and $R^5$=CH$_3$, $C_6H_4$—CH$_3$, with a strong base, whose amount is at least equal to the stoichiometric amount.

6. Process as claimed in claim 5, wherein the strong base is selected from the group consisting of hydroxides, alkoxides, carbonates, bicarbonates, hydrides of alkaline or alkaline-earth metals, as well as of tetraalkylammonium, tetraalkylarsonium or tetraalkylphosphonium bases.

7. Aryl-alkyl ketals of formula

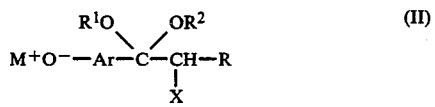

wherein Ar=phenyl or naphthyl, unsubstituted or substituted with $C_1$–$C_3$ alkyl, OH or $C_1$–$C_3$ alkoxyl, halogen or phenyl; R=H or straight or branched $C_1$–$C_6$ alkyl; $R^1$ and $R^2$, which are the same or different, are a $C_1$–$C_6$ alkyl group, a $C_3$–$C_6$ alkenyl or alkynyl group, or bound together, form a saturated or unsaturated heterocyclic ring comprising from 3 to 7 carbon atoms; X=Cl, Br, I; M is the counter-ion of the phenolate, preferably selected from the group consisting of alkaline and alkaline-earth cations, tetraalkylammonium, tetraalkylarsonium, or tetraalkylphosphonium groups.

* * * * *